United States Patent [19]

Stolz et al.

[11] Patent Number: 5,309,229
[45] Date of Patent: May 3, 1994

[54] DUAL OPTIC VIDEO DISPLAY BEARING INSPECTION SYSTEM

[75] Inventors: Kenneth Stolz, Duncansville; Gerhard A. Thelen, St. Davids, both of Pa.; Paul G. Steets, Marlton, N.J.

[73] Assignee: Consolidated Rail Corporation, Philadelphia, Pa.

[21] Appl. No.: 761,730

[22] Filed: Sep. 18, 1991

[51] Int. Cl.[5] .............................. H04N 7/18
[52] U.S. Cl. .................... 348/128; 356/237; 348/136
[58] Field of Search .............. 358/106, 107, 101, 100, 358/98, 93; 356/237, 239, 240, 241; 250/572, 562, 208.1; H04N 7/18

[56] References Cited

U.S. PATENT DOCUMENTS

| | | | |
|---|---|---|---|
| 3,830,969 | 8/1974 | Hofstein | 358/106 |
| 4,315,688 | 2/1982 | Pryor | 356/236 |
| 4,576,482 | 3/1986 | Pryor | 358/107 |
| 4,644,394 | 2/1987 | Reeves | 358/106 |
| 4,672,437 | 6/1987 | Casper | 358/106 |
| 4,993,836 | 2/1991 | Furuhashi et al. | 358/107 |
| 5,012,116 | 4/1991 | Russell | 250/572 |

Primary Examiner—James J. Groody
Assistant Examiner—Michael H. Lee
Attorney, Agent, or Firm—Woodcock Washburn Kurtz Mackiewicz & Norris

[57] ABSTRACT

Methods and apparatus for inspecting surfaces are disclosed. The present invention provides a system which is particularly useful for inspecting the inner race of a bearing and uses two video probes to create dual displayed views of the inner surface. The bearing is slowly rotated and the entire surface of the inner race is visually inspected by viewing the images collected by the video probes. Preferably, a motorized stand and frame are provided that automatically rotate the bearing and automatically insert the video probes into the bearing respectively. The magnification provided by the video probes permits the detection of flaws invisible to the human eye, and in certain embodiments a scale on or adjacent to the video images is also provided so that the size of the defects viewed can also be accurately determined.

12 Claims, 1 Drawing Sheet

DUAL OPTIC VIDEO DISPLAY BEARING INSPECTION SYSTEM

The present invention relates to methods and apparatus for inspecting the condition of bearings. More particularly, the present invention relates to the visual inspection of the rolling elements and races of bearings using a video system.

BACKGROUND OF THE INVENTION

Bearings are a vital part of innumerable types of equipment. Ball bearings and roller bearings can be found in nearly every type of machine and device with rotating parts. Roller bearings are frequently specified when shock and impact loads are present, or when a large bearing is needed. Both ball and roller bearings generally consist of at least four elements: inner and outer bearing rings (also known as races), the rollers (or balls) and a cage (or bearing separator). The "cone" of a bearing consists of three of these elements: the inner ring, rollers and separator. The construction and function of ball and roller bearing assemblies is familiar to those of ordinary skill.

Although bearings are precisely constructed, failure after a certain point is inevitable. Such failure may be caused by foreign objects or due to flaws in the bearing components themselves. Other failure modes are simply caused by wear. However, if the advent of failure is discovered, most bearings can be removed from service and refurbished or rebuilt prior to a catastrophic failure that would at the very least require replacement of the bearings. It has therefore become recognized that bearings can be visually inspected and the amount of wear can be determined both qualitatively and quantitatively to permit a decision to be made about the remaining useful life of a bearing.

A critically important application of bearings and bearing inspections is found in rail cars. The loads carried by the wheels and axles of rail cars are enormous and the efficiency of the rolling stock is directly affected by the condition of the bearings. For this reason, the Association of American Railroads (AAR) has set forth a detailed set of requirements and standards for the inspection of roller bearings. See Association of American Railroads, Mechanical Division, Roller Bearing Manual, Section 1, pp. H-II-1 through H-II-16 (Oct. 1, 1989), which is incorporated by reference as if fully set forth herein. The definitions and terms set forth in the above-referenced AAR Manual are hereby adopted for purposes of describing the present invention. However, the use of the present invention is not meant to be limited to the types of bearings described in the AAR Manual.

Presently, the standard method used for inspecting roller bearing cones is by visual inspection. To perform the inspection, a roller bearing cone is placed on a back lit inspection stand. The inspection stand holds the cone in a manner that permits it to be rotated, and illuminates the bearing from behind to permit an inspector to view portions of the bearing. The inner ring is then rotated and the rollers and inner raceway are visually inspected by observing the back lit areas. However, certain areas of the inner raceway are indented and cannot be seen using the back-lit method since they are located outside the line of sight of the inspector. In order to inspect those areas of the inner raceway that cannot be seen, a pointed feeler gage is held over the area while the cone is being rotated. A defect, e.g., a spall, will cause the feeler gage to transmit a slight mechanical vibration to the hand of the inspector. By virtue of experience, the inspector can determine whether the defect indicated is condemnable and constitutes a reason to repair the bearing, or scrap the cone if the defect cannot be repaired. There are two main disadvantages associated with the visual procedures currently used to inspect bearings. First, the back-lit viewing stands do not provide a clear view of every portion of the critical components of the bearing. Second, those portions of the inspection carried out using a feeler gage rely upon the sensitivity, experience and the subjective judgment of the inspector.

One attempt to provide improved rail car bearing inspections is known as the "Santa Fe" method, which involves a device analogous to a phonograph turntable that rotates a bearing while a stylus traces a path across the race surfaces. The deflections of the stylus provide an analog signal that can be displayed on an oscilloscope as a measure of the relative smoothness of the path traced by the stylus. Using this system, it is possible to detect certain types of flaws by quantifying the permissible level of deflection as measured on the oscilloscope scale. However, since this method cannot detect those types of flaws that do not exhibit surface deformations, it can only be used to reject bearings prior to undertaking the abovedescribed manual/feeler gage inspection.

Thus, there exists a need to provide improved methods and apparatus for inspecting bearings. It would be desirable to visually inspect the entire surfaces of critical bearing components. It would also be desirable to provide an inspection procedure that did not rely on the subjective judgment of the inspector to determine the degree to which a defect affects a bearing on the basis of "feel." Accordingly, it is an object of the present invention to provide an optical display system for inspecting bearings. It is a further object of the present invention to permit bearing inspections to be carried out more rapidly and with greater accuracy, thereby increasing the overall efficiency of the bearing inspection and rebuilding operation.

SUMMARY OF THE INVENTION

Accordingly, the present invention provides methods of inspecting a surface of an object, wherein the surface being inspected is bidden so as to be blocked from view in a single line of sight. The methods comprise the steps of inserting a video probe into an object such that it can view at least a portion of the surface to be inspected and then inserting a second video probe into the object such that it may view the portion of the surface to be inspected that was not within the field of view of the first video probe. The video signals collected by these video probes are then displayed. Preferably, two separate video monitors are provided to display the images generated by the two video probes simultaneously. The surface being inspected and the video probes are then moved relative to one another such that the entire surface to be inspected is visually reviewed as displayed images.

As particularly applied to methods of inspecting the surface of a roller bearing the present invention provides methods comprising inserting a first and second video probe as explained above and mounting the bearing on a rotating bearing stand. In a preferred embodiment of the present invention, the bearing stand is motorized and will automatically rotate the bearing. The displayed images are reviewed for defects and as the bearing rotates, the entire surface of the inner race is eventually displayed and has been inspected.

The present invention also provides apparatus for inspecting a surface of a roller bearing comprising a first and second video probe, a rotating bearing stand and one or more monitors for displaying the images collected by the first and second video probes. In a preferred embodiment, a motor is provided to automatically rotate the bearing surface being inspected and a motorized frame is also provided in certain embodiments to move one or both of the video probes into and out of the bearing assembly. Preferably, an operator control panel is provided that will permit the video images to be controlled, as well as the motorized bearing stand and motorized frame that positions the video probes. In certain embodiments of the present invention a scale is provided on or adjacent to the projected images in order to permit the size of the defects being viewed to be accurately determined.

DETAILED DESCRIPTION OF THE PREFERRED EMBODIMENTS

Figure 1:
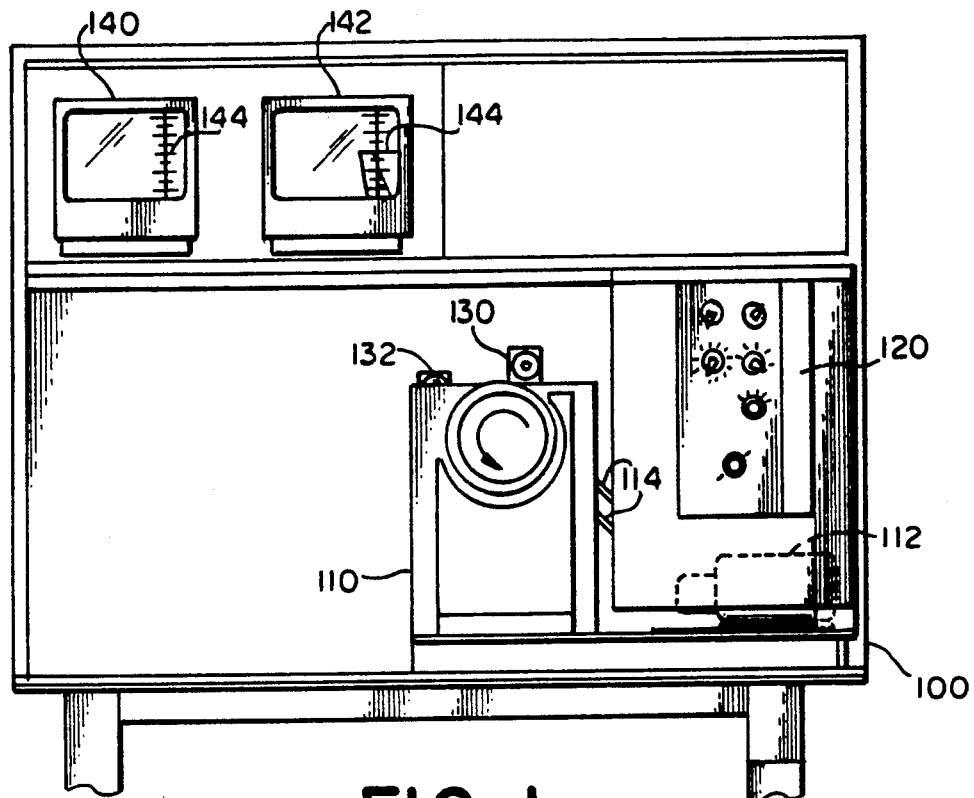
FIG. 1 is a front elevation view of a video inspection apparatus made in accordance with the present invention.
Figure 2:
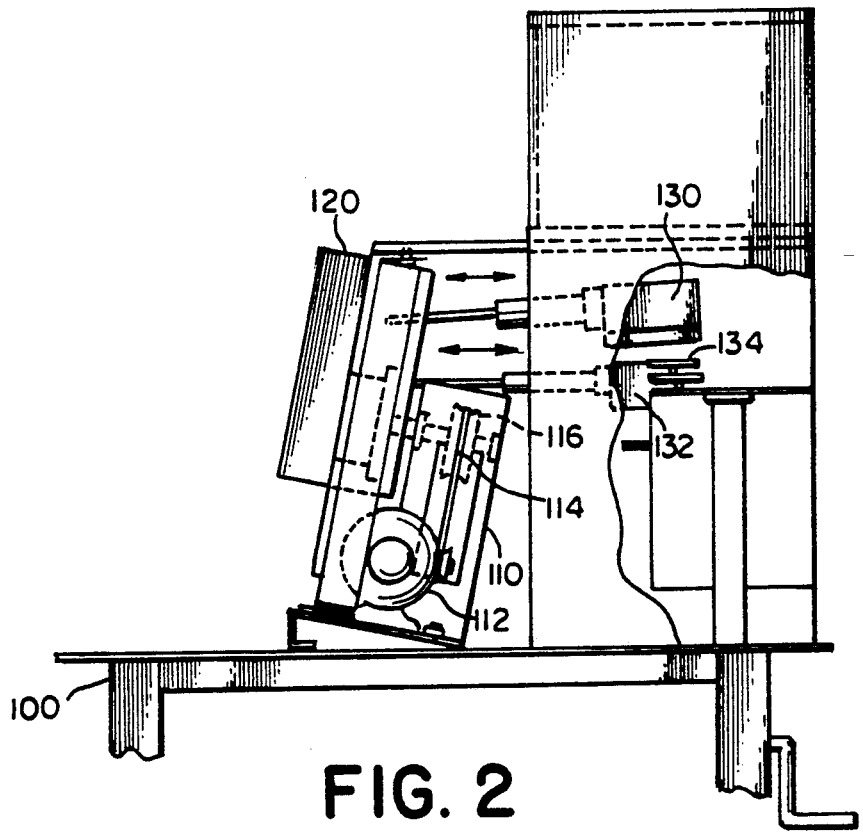
FIG. 2 is a side elevation view of the video inspection apparatus depicted in FIG. 1.

Referring now to FIG. 1, there is shown a front view of a dual display bearing inspection stand 100 made in accordance with the present invention. The present invention utilizes a bearing inspection stand 110 that permits the bearing being inspected to be rotated, however, unlike the prior art method described above, no back-lighting is used. The inspection stand 110 of the present invention is most preferably connected to a motor 112 via belts and pulleys 114,116 that permit the bearing being inspected to be rotated automatically at a controlled rate of speed. Controls on an operator panel 120 permit the rotation of the bearing to be started and stopped, and the speed adjusted.

Instead of relying on the inspector's vision, the apparatus of the present invention preferably includes at least two video probes 130,132 that are positioned to provide views of the surfaces of interest, as will be further explained below. The video probes 130 used in the present invention are preferably of the fiber optic type such as the Olympus DES Fiberscope distributed by Olympus Corporation, Industrial Fiberoptics Division, 4 Nevada Drive, Lake Success, N.Y., U.S.A. 11042-1179. However, many other types of borescopes or similar optical apparatus can provide the function of the video probes 130,132 to permit the observation and inspection of the inside of structures that cannot be observed directly from the outside. In a preferred embodiment of the present invention, the video probes 130,132 are attached to a motorized frame 134 controlled by the operator panel 120 and can be moved relative to the bearing inspection stand 110.

The video output signals of the video probes 130,132 are preferably transmitted, respectively, to dual video display monitors 140,142. As will be recognized by those of ordinary skill, the choice of video monitors 140,142 depends upon the application, i.e., the type of bearing inspection being undertaken, and also upon the requirements of the video probes 130,132. Additionally, a single monitor using a split screen or switching screen may also be useful in certain embodiments. The embodiment of the present invention described herein is outfitted with two JVC Model TM-9U(A) Color Video Monitors, distributed by JVC Professional Products Company, 41 Slater Drive, Elmwood Park, N.J., U.S.A. 07407. As explained below, in preferred embodiments of the present invention, the views provided by the video monitors 140,142 include a scale 144, either as a transmitted image or physically placed on or adjacent to the screen of the video monitors 140,142.

In accordance with the present invention, a first video probe 130 is inserted into a bearing or a portion of a bearing, e.g., a bearing case, and placed on the inspection stand 110. Most preferably, the first video probe 130 is inserted between the roller cage and the inner race and has at least a portion of the surface being inspected within its field of view. A second video probe 132 is then placed within the bearing. Preferably, the second video probe 132 is placed to view those portions of the bearing that are not within the field of view of the first video probe 130 so that the entire surface being inspected is in view. The placement of the second video probe 132 is most preferably accomplished automatically using the movement of the motorized frame 134 described above. The second video probe 132 will thus be able to view the area that previously had been inspected using a feeler gage. The two views generated by the video probes 130,132 are preferably simultaneously displayed on the monitors 140,142, and the inner ring of the bearing is slowly rotated, preferably using the motor 110, and belt and pulley system 112,114 described above.

To inspect bearings using the present invention, the operator simply observes the images presented by the monitors 140,142. Since they provide an accurate view of the actual surface, the visual detection of spalling, cracking, Brinelling and other defects is facilitated. In preferred embodiments of the present invention the images shown on the monitors 140,142 are enlarged, preferably to about 100×, permitting greater accuracy and the detection of minute flaws that cannot be detected with the naked eye. Additionally, in a preferred embodiment, the screens of the monitors 140,142 are marked with scales 142 that permit the operator to determine if the sizes of the defects shown exceed the maximum values set by the above-referenced Association of American Railroads Manual. As with the image itself, these scales 142 are depicted in an enlarged manner and further enhance the accuracy of the inspection process.

In use, it has been found that an inspector can view the images presented by the monitors 140,142 without undue eye strain while the bearing is being rotated at a rate that permits a shorter overall inspection time than found in prior art systems. Moreover, the automated aspects of the present invention reduce fatigue and thus increase accuracy. The combination of all these advantageous features results in a system whereby the throughput, i.e., the number of bearings inspected per unit time, is significantly increased while also obtaining a gain in quality.

Although certain embodiments of the present invention have been described above in detail, the present invention is not meant to be limited thereby. Those of ordinary skill, upon review the descriptions set forth above, will immediately realize that there are numerous variations, adaptations and modifications that can be made to the methods and apparatus described above. Moreover, the present invention is applicable to many types of bearings and their component parts including casings, fittings and the like that must be inspected while presenting surfaces that are not easily viewed with the eye. Accordingly, reference should be made to the appended claims to determine the scope of the present invention.

What is claimed is:

1. A method of inspecting a surface of an object, wherein the surface being inspected is hidden so as to be blocked from view in a single line of sight, the method comprising the steps of:
   inserting a first video probe into the object, the first video probe disposed to view at least a portion of the surface being inspected;
   inserting at least a second video probe into the object, the second video probe disposed to view at least a portion of the surface being inspected not within the field of view of the first video probe;
   displaying an image collected by the first and second video probes; and
   moving the surface and the first and second video probes relative to one another,
   whereby the entire surface to be inspected is visually reviewed as a displayed image.

2. The method of claim 1, wherein the object is a substantially circular bearing assembly and the first and second video probes are disposed such that the combined view includes the entire inner surface of the inner race of the bearing assembly.

3. The method of claim 1 wherein the step of moving the surface and the first and second video probes relative to one another is carried out automatically.

4. The method of claim 1, wherein the step of displaying an image comprises connecting the first video probe to a first monitor and connecting the second video probe to a second monitor.

5. The method of claim 1, wherein the step of displaying an image comprises displaying a scale for determining the size of an object shown in the image.

6. The method of claim 5, wherein the scale is projected on to the image.

7. The method of claim 5, wherein the scale is physically located adjacent the image.

8. The method of claim 1, wherein at least one of the steps of inserting the first and second video probes is carried out automatically.

9. A method of inspecting a surface of a bearing assembly, the method comprising the steps of:
   inserting a first video probe into the bearing assembly, the first video probe disposed so as to view at least a portion of the surface being inspected;
   mounting the bearing on a rotating bearing stand;
   inserting a second video probe into the bearing assembly, the second video probe disposed so as to view at least a portion of the surface being inspected not within the view of the first video probe;
   displaying an image collected by the first and second video probe; and
   rotating the bearing to move the surface being inspected relative to the first and second video probes,
   whereby the entire surface to be inspected is visually reviewed as a displayed image.

10. The method of claim 9, wherein the first and second video probes are disposed such that the combined view includes the entire inner surface of the inner race.

11. The method of claim 9, wherein the step of rotating the bearing is carried out automatically.

12. The method of claim 9, wherein the step of inserting the second video probe is carried out automatically.

* * * * *